US005496804A

United States Patent [19]
Reed et al.

[11] Patent Number: 5,496,804
[45] Date of Patent: Mar. 5, 1996

[54] METHOD FOR TREATING TAXOL SIDE-EFFECTS WITH G-CSF

[75] Inventors: Eddie Reed, Germantown; Elise Kohn, Olney; Gisele Sarosy, Silver Spring, all of Md.

[73] Assignee: The United States of America as represented by the Department of Health and Human Services, Washington, D.C.

[21] Appl. No.: 342,797

[22] Filed: Nov. 21, 1994

Related U.S. Application Data

[63] Continuation of Ser. No. 28,411, Mar. 9, 1993, abandoned.
[51] Int. Cl.$^6$ .................................................. A61K 37/00
[52] U.S. Cl. .............................................. 514/12; 514/922
[58] Field of Search ........................................ 514/12, 922

[56] References Cited

U.S. PATENT DOCUMENTS

| | | | |
|---|---|---|---|
| 4,942,184 | 7/1990 | Haugwitz et al. | 514/449 |
| 4,958,009 | 9/1990 | Bjorn et al. | 530/389 |
| 4,961,926 | 10/1990 | Garbrilore | 424/85.1 |
| 5,104,651 | 4/1992 | Boone et al. | 424/85.1 |
| 5,157,049 | 10/1992 | Haugwitz et al. | 514/449 |

OTHER PUBLICATIONS

Antman, "G–CSF and GM–CSF in Clinical Trials," *Yale J. Biol. Med.*, 63, 387–410 (1990).
Bronchud et al., "Phase I/II study of recombinant human granulocyte colony–stimulating factor in patients receiving intensive chemotherapy for small cell lung cancer," *Br. J. Cancer*, 56, 809–813 (1987).
Brown et al., "A Phase I Trial of Taxol Given by a 6–Hour Intravenous Infusion," *J. Clin. Oncol.*, 9, 1261–1267 (1991).
Budman et al., "Initial Findings of CALGB 8541: A Dose and Dose Intensity Trail of Cyclophosphamide (C), Doxorubicin (A), and 5–Fluorouracil (F) as Adjuvant Treatment of Dtage II, Node +, Female Breast Cancer," *Proc. Am. Soc. Clin. Oncol.*, 11, Abst. #29, 51 (1992).
Buller et al., "CA 125 regression: A model for epithelial ovarian cancer response," *Am. J. Obstet. Gynecol.*, 165, 360–367 (1991).
Chabner, "Taxol," *Principles & Practice on Oncology Updates*, 5, 1–19 (1991).
Chang et al., "Phase II Study of Taxol in Patients with Stage IV Non–Small Cell Lung Cancer; The Eastern Cooperative Oncology Group Results," *Proc. Am. Soc. Clin. Oncol.*, 11, Abst. #981, 293 (1992).
Crawford et al., "Reduction by Granulocyte Colony–Stimulating Factor of Fever and Neutropenia Induced by Chemotherapy in Patients with Small–Cell Lung Cancer," *New Engl. J. Med.*, 325, 164–170 (1991).
DeVita et al., "The Chemotherapy of Lymphomas: Looking Back, Moving Forward," *Cancer Res.*, 47, 5810–5824 (1987).
DeVita, "The influence of information on drug resistance on protocol design," *Annals of Oncology* 2, 93–106 (1991).
DeVita et al., "Treatment of Hodgkin's Disease," *J. Natl.*

*Cancer Inst. Monographs* No. 10 (1990).
Donehower et al., "Phase I Trail of Taxol in Patients with Advanced Cancer," *Cancer Treat. Rep.* 71, 1171–1177 (1987).
Einzig et al., "Phase II study of taxol in patients with advanced ovarian cancer," *Proc. Am. Assoc. Cancer Res.*, 31, Abst. #1114, 187 (1990).
Einzig et al., "Taxol: A new agent active in melanoma and ovarian cancer," *Cancer Treat. Res.*, 58, 89–100 (1991).
Einzig et al., "A Phase II Study of Taxol in Patients with Malignant Melanoma," *Invest. New Drugs*, 9, 59–64 (1991).
Einzig et al., "Phase II Trail of Taxol in Patients with Metastatic Renal Cell Carcinoma," *Cancer Invest.* 9, 133–136 (1991).
Forastiere et al., "Phase I Trail of Taxol and Cisplatin+ G–CSF in Solid Tumors," *Proc. Am. Soc. Cancer Oncol.*, 11, Abst. #289, 117 (1992).
Frost & Sullivan Reports, "Colony–stimulating Factors (CSF)," in: *The U.S. Market for Cancer Therapy Products*, vol. I, 142–149, (Frost & Sullivan, Inc., New York, 1991).
Gabrilove et al., "Effect of granulocyte colony–stimulating factor on neutropenia and associated morbidity due to chemotherapy for transitional–cell carcinoma of the urothelium," *New Engl. J. Med.*, 318, 1414–1422 (1988).
Holmes et al., "Phase II Trail of Taxol, an Active Drug in the Treatment of Metastatic Breast Cancer," *J. Natl. Cancer Inst.*, 83, 1797–1805 (1991).
Holmes et al., "Phase II Study of Taxol and Doxorubicin with G–CSF in Patients Without Prior Chemotherapy for Metastatic Breast Cancer," *Proc. Am. Soc. Clin. Oncol.*, 11, Abst. #66, 60 (1991).
Hrynuik et al., "Analysis of Dose Intensity for Adjuvant Chemotherapy Trials in Stage II Breast Cancer," *J. Clin. Oncol.* 4, 1162–1170 (1986).
Kris et al., "Phase I Trial of Taxol Given as a 3–Hour Infusion Every 21 Days," *Cancer Treat. Rep.* 70, 605–607 (1987).
Kumar, "Taxol induced Polymerization of Purified Tubulin," *J. Biol. Chem.*, 256, 10435–10441 (1981).
Legha et al., "A Phase II Trial of Taxol in Metastatic Melanoma," *Cancer*, 65, 2478–2481 (1990).
Levin et al., "The Application of Dose Intensity to Problems in Chemotherapy of Ovarian and Endometrial Cancer," *Semin. Oncol.*, 14 (suppl. 4), 12–19 (1987).
Levin et al., "Dose Intensity Analysis of Chemotherapy Regimens in Ovarian Carcinoma," *J. Clin. Oncol.* 5, 756–767 (1989).
Lipton et al., "Taxol produces a predominantly sensory neuropathy," *Neurology* 39, 368–373 (1989).

(List continued on next page.)

*Primary Examiner*—Theodore J. Criares
*Attorney, Agent, or Firm*—Leydig, Voit & Mayer, Ltd.

[57] ABSTRACT

A method of treating a host using taxol comprising administering granulocyte colony-stimulating factor to the host being treated with taxol. The present inventive method allows for increased levels of taxol to be administered to the host in the treatment of various conditions, particularly with respect to ovarian tumors.

15 Claims, No Drawings

OTHER PUBLICATIONS

Lund et al., "Comparison of the Predictive Power of Different Prognostic Indices for Overall Survival in Patients with Advanced Ovarian Carcinoma," *Cancer Res.*, 50, 4626–4629 (1990).

Malkasian et al., "Prognostic significance of histologic classification and grading of epithelial malignancies of the ovary," *An. J. Obstet. Gynecol.*, 149, 274–284 (1984).

Markman et al., "Responses to Second–Line Cisplatin–Based Intraperitoneal Therapy in Ovarian Cancer: Influence of a Prior Response to Intravenous Cisplatin," *J. Clin. Oncol.*, 9, 1801–1805 (1991).

Mayer et al., "Comparative Evaluation of Intensitve Post–Remission Therapy with Different Dose Schedules of Ara–C in Adults with Acute Myeloid Leukemia (AML): Initial Results of a CALGB Phase III Study," *Proc. Am. Soc. Clin. Oncol.* 11, Abst. #853, 261 (1992).

McGuire et al., "Taxol: A Unique Antineoplastic Agent with Significant Activity in Advanced Ovarian Epithelial Neoplasms," *Ann. Intern. Med.* 111, 273–279 (1989).

Omura et al., "Long–Term Follow–Up and Prognostic Factor Analysis in Advanced Ovarian Carcinoma: The Gynecologic Oncology Group Experience," *J. Clin. Oncol.*, 9, 1138–1150 (1991).

Ozols et al., "Summary of Symposium: Biology and Therapy of Ovarian Cancer," *Semin. Oncol.*, 18, 297–306 (1991).

Reed et al., "Suramin in Advanced Platinum–resistant Ovarian Cancer," *Eur. J. Cancer*, 28A, 864–866 (1992).

Reed et al., "5–Fluorouracil and Leucovorin in Platinum–Refractory Advanced Stage Ovarian Carcinoma," *Gynecol. Oncol.*, 46, 326–329.

Roesler et al., "In vitro functions of neutrophils induced by treatment with rhG–CSF in severe congenital neutropenia," *Eur. J. Haematol.*, 46, 112–118 (1991).

Rothenberg et al., "Changing concepts in the management of epithelial ovarian and cervical cancers," *Med. J. of Australia*, 148, 354–363 (1988).

Rowinsky et al., "Phase I and Phamacodynamic Study of Taxol in Refractory Acute Leukemias," *Cancer Res.*, 49, 4640–4647 (1989).

Rowinsky et al., "Taxol: A Novel Investigational Antimicrotubule Agent," *J. Natl. Cancer Inst.*, 82, 1247–1259 (1990).

Rowinsky et al., "Cardiac Disturbances During the Administration of Taxol," *J. Clin. Oncol.*, 9, 1704–1712 (1991).

Sarosy et al., "Taxol Dose Intensification in Patients with Recurrent Ovarian Cancer," *Proc. Am. Soc. Clin. Oncol.*, 11, Abst. #716, 226 (1992).

Scarffe et al., "Clinical studies of granulocyte colony stimulating factor," *Cancer Surveys*, 9, 115–130 (1990).

Schiff et al., "Promotion of microtubule assembly in vitro by taxol," *Nature*, 277, 655–667 (1979).

Souza et al., "Recombinant Human Granuloctye Colony–Stimulating Factor: Effects on Normal and Leukemic Myeloid Cells," *Science*, 232, 61–65 (1986).

Thigpen et al., "Phase II trial of taxol as second–line therapy for ovarian carcinoma," *Proc. Am. Soc. Clin. Onc.*, 9, Abst. #604, 156 (1990).

Weiss et al., "Hypersensitivity Reactions From Taxol," *J. Clin. Oncol.*, 8, 1263–1268 (1990).

Welte et al., "Purification and biological characterization of human pluripotent hematopoietic colony stimulating factor," *Proc. Natl. Acad. Sci.*, 82, 1526–1530 (1985).

Wiernik et al., "Phase I Trial of Taxol Given as a 24–Hour Infusion Every 21 Days: Responses Observed in Metastatic Melanoma," *J. Clin. Oncol.*, 5, 1232–1239 (1987).

Wiernik et al., "Phase I Clinical and Pharmacokinetic Study of Taxol," *Cancer Res.* 47, 2486–2493 (1987).

Yoshida et al., "Effect of Granulocyte Colony–Stimulating Factor on Neutropenia Due to Chemotherapy for Non–Hodgkin's Lymphoma," *Cancer*, 66, 1904–1909 (1990).

Young et al., "Cancer of the Ovary," in: *Cancer Principles and Practice of Oncology*, DeVita et al., eds., 1162–1196 (J. B. Lippincott Co., Philadelphia, 1989).

METHOD FOR TREATING TAXOL SIDE-EFFECTS WITH G-CSF

This is a continuation of application 08/028,411 filed on Mar. 9, 1993 now abandoned.

TECHNICAL FIELD OF THE INVENTION

The present invention relates generally to an improved method for treating a host with taxol. More specifically, the present inventive method pertains to the treatment of cancerous tumors in humans, especially ovarian tumors, with taxol.

BACKGROUND OF THE INVENTION

Significant strides have been made in the treatment of advanced stage cancers over the past few years. One of these advances centers around the introduction of cisplatin into treatment regimens for ovarian cancer. Despite such advances, however, the number of patients experiencing long-term disease-free periods after receiving such platinum-based therapy remains under 20 percent (Young et al., "Cancer Of The Ovary" in *Cancer Principles and Practice of Oncology* (DeVita et al., Eds., J. B. Lippincott Co., Philadelphia), 1162–96 (1989); Rothenberg et al., *Med. J. Australia*, 148, 354–63 (1988)). While these results are encouraging, they nevertheless underscore the need for the discovery of more effective agents and regimens useful in treating solid cancerous tumors.

Taxol has been identified as one such new agent. This agent is derived from the bark of the Western Yew tree, *taxus brevifolia* (Chabner, *PPO Update*, 5 (9), 1–10 (1991); Rowinsky et al., *J. Nat'Cancer Inst.*, 82, 1247–1259 (1990)). Studies to date have indicated that taxol within a dose range of 110 to 200 $mg/m^2$ has produced objective responses in about 30 percent of patients having cisplatin-sensitive and cisplatin-resistant advanced stage epithelial ovarian cancer (McGuire et al., *Ann. Intern. Med.*, 11, 273–79 (1989); Thigpen et al., *Proceedings ASCO*, 9, 156 (Abst. 604) (1990); Einzig et al, *Proceedings AACR*, 31, 187 (Abst. 1114) (1990)). Indeed, taxol is the only agent with proven efficacy for patients with platinum-resistant ovarian cancer.

However, despite taxol's promise, there is a limit to the amount of taxol that can be used in any treatment regimen. More specifically, when taxol is administered in a treatment regimen for solid tumors, patients experience myelosuppression i.e., bone marrow suppression which includes neutropenia, anemia, and thrombocytopenia, at elevated taxol levels. This myelosuppression is dose-limiting, hence the maximum quantity of taxol that is recommended to be used in the treatment of solid tumors is 175 mg per square meter of body area every 21 days ($mg/m^2$/ 21 days) (Donehower et al., *Cancer Treat. Rpt.*, 71, 1171–77 (1987); Wiernik et al., *Cancer Res.*, 47, 2486–93 (1987); Wiernik et al., *J. Clin. Oncol.*, 5, 1232–39 (1987)).

Other problems in addition to myelosuppression appear when dosage levels of taxol over the previously identified maximum are administered. As the taxol dosage level is increased to levels above about 175–200 $mg/m^2$/ 21 days, a further dose-limiting toxicity, mucositis, is encountered. Mucositis is an inflammation of the lining of the gastrointestinal tract which may result in mouth sores, painful diarrhea, and rectal soreness. Eventually, with yet higher dosage levels of taxol, e.g., above about 300 $mg/m^2$/ 21 days, severe neurotoxicity in the form of peripheral neuropathy is experienced (Rowinsky et al., *Cancer Res.*, 49,4640–47 (1989); Lipton et al., *Neurology*, 39,368–73 (1989)).

The aforesaid potentially severe consequences which arise when taxol is administered at dosages above about 175 $mg/m^2$/ 21 days have prevented even the clinical investigation of the therapeutic effect of taxol at dosages in excess of that level.

Accordingly, there exists a need for a means to alleviate or prevent the adverse side-effects attendant the administration of taxol in high doses so as to enable an evaluation of the therapeutic effects of taxol at dosage levels above the dose-limiting amount presently able to be safely administered. Similarly, there is a need for a method of providing a relatively safe and effective regimen using taxol for the treatment of cancerous solid tumors, particularly ovarian tumors, without the attendant side-effects of myelosuppression, mucositis, and other toxicities.

These needs are satisfied with the method of the present invention. In particular, it is an object of the present invention to provide a means of enabling the evaluation of the therapeutic benefits of taxol while alleviating or preventing myelosuppression, mucositis, and other toxicities. It is a further object of the present invention to provide a safe and effective regimen utilizing taxol for the treatment of cancerous tumors.

These and other objects and advantages of the present invention, as well as additional inventive features, will be apparent from the description of the invention provided herein.

BRIEF SUMMARY OF THE INVENTION

The present invention provides a method of treating a host using taxol comprising administering granulocyte colony-stimulating factor to a host being treated with taxol. The invention advantageously provides for the treatment of a host with taxol in an amount greater than currently being used and which would otherwise be sufficient to cause myelosuppression or mucositis if not administered in conjunction with the administration of a granulocyte colony-stimulating factor. In accordance with the present invention, granulocyte colony-stimulating factor is administered in an amount effective to alleviate or prevent myelosuppression (e.g., neutropenia), and most preferably, mucositis. The invention provides an improved method for the treatment of cancerous tumors, e.g., breast, lung, and particularly ovarian tumors, with taxol.

DESCRIPTION OF THE PREFERRED EMBODIMENTS

The method of the present invention provides a means for treating a host who is undergoing therapy with the pharmaceutical drug taxol. In particular, the present inventive method comprises administering granulocyte colony-stimulating factor (G-CSF) to a host being treated with taxol. The term taxol as used herein and in the appended claims encompasses taxol per se as well as all water-soluble derivatives thereof, particularly water-soluble taxol derivatives, such as, for example, 2'-succinyl-taxol, 2'-succinyl-taxol triethanolamine, 2'-glutaryl-taxol, 2'-glutaryl-taxol triethanolamine salt, 2'-with N-(dimethylaminoethyl) glutamide, and 2'-O-ester with N-(dimethylaminoethyl) glutamide hydrochloride salt. Examples of taxol compounds and methods for their preparation are set forth in U.S. Pat. No. 4,942,184. U.S. Pat. No. 5,104,651 provides further information regarding G-CSF and pharmaceutical formulations thereof. G-CSF is available from Amgen, Inc. of Thousand Oaks, Calif.

The present inventive method advantageously provides a means by which taxol may be administered to a host during a treatment regimen in an amount sufficient to cause myelosuppression (e.g., neutropenia with or without fever) or mucositis if not administered in conjunction with the administration of G-CSF. In other words, taxol can now be administered in excess of the current dose-limiting amount, i.e., in excess of about 175 mg/m$^2$/ 21 days.

Generally, G-CSF is administered to the host being treated with taxol in an amount effective to either alleviate or prevent myelosuppression or mucositis. The amount of G-CSF which will provide the aforesaid benefits will vary somewhat depending on the particular host.

5 Typically, the amount of G-CSF administered will be about 5 µg/kg/day and more typically from about 10 to about 20 µg/kg/day for at least about seven days of each 21 day taxol treatment cycle.

The present invention further provides a novel variable dosing regimen for G-CSF wherein the G-CSF dose intensity is varied based upon the symptoms exhibited by the patient during taxol treatment. For example, if the patient develops neutropenia during a cycle of therapy, instead of addressing this in the conventional manner—by reducing the taxol dose intensity after that cycle of therapy—the present inventive method calls for an increase in G-CSF dose intensity during the subsequent cycle. This enables the taxol dose intensity to be maintained at the same level during the subsequent cycle. In view of this discovery, and assuming, for example, neutropenia is experienced by a patient, the G-CSF dose intensity, which would typically be administered at a level of about 10 µg/kg/day for a patient receiving taxol at a dosage level of about 250 mg/m$^2$/ 21 days, would advantageously be increased to a level ranging from about 10–20 µg/kg/day, and preferably to a level ranging from about 15–20 µg/kg/day. This increase would allow the taxol dose intensity in a subsequent cycle or cycles to remain at the 250 mg/m$^2$/ 21 days level.

A typical taxol treatment regimen in accordance with the present invention therefore comprises administering taxol once every three weeks in conjunction with the daily administration of G-CSF. Preferably, the host is treated with taxol in an amount of about 200 to about 250 mg/m$^2$/ 21 days, and G-CSF is administered in an amount of about 10 to about 20 µg/kg/day for about seven days of the taxol cycle. If the CSF dose of 10 µg/kg/day is poorly tolerated (as occurs in about 5% of patients), the G-CSF dose can be reduced to about 5 µg/kg/day.

While the method of the present invention is effective with respect to any use of taxol, it is particularly well-suited in treating cancerous tumors in a host, especially ovarian, breast, and lung cancers. The present inventive method is particularly useful in the treatment of cancerous ovarian tumors.

The present invention provides for the raising of the current standard dose-limiting level of taxol from about 175 mg/m$^2$/ 21 days to about 250 mg/m$^2$/ 21 days and perhaps as high as 300 mg/m$^2$/ 21 days. Moreover, the invention provides a means by which the typical or "standard" dose of taxol can be increased from the current level of about 135 mg/m$^2$/ 21 days to about 250 mg/m$^2$/ 21 days. The present invention, therefore, provides for an approximately 40–85% increase in the amount of taxol that can be safely administered to a host. This increase in the level of taxol corresponds to an increase in the objective response of cancerous tumors and, in particular ovarian cancer. With the "standard" dose of taxol, the objective response rate is about 30%. When administering taxol at a dosage of about 250 mg/m$^2$/ 21 days, the objective response rate is about 50% (a 67% increase in the response rate).

It was at the 300 mg/m$^2$/ 21 days taxol level that, even with the administration of G-CSF, the dose-limiting symptoms of peripheral neuropathy of grade 3 were detected. Grade 3 peripheral neuropathy is defined for the purposes of describing the present invention as the occurrence of a functional deficit (e.g., difficulty in the use of the hands or unsteadiness of gait) accompanied by diminution in reflexes and distal dysesthesia or sensory loss. While substantial myelosuppression can be observed with the administration of such high dose levels of taxol in accordance with the present invention, such myelosuppression is not dose-limiting. Moreover, mucositis is rarely observed at these higher taxol levels achieved as a result of the present invention.

The following examples further illustrate the present invention and should not be construed in any manner to limit its scope.

EXAMPLE 1

This example illustrates the use of the present invention in treating cancerous tumors and demonstrates that the present invention allows for increased taxol administration to those being treated for cancer.

Patients with histologically proven epithelial ovarian cancer with bidimensionally measurable disease were candidates for the study. Eligibility criteria included: (1) no more than two prior treatment regimens; (2) performance status of Eastern Cooperative Oncology Group (ECOG) 2 or better; (3) preexisting peripheral neuropathy of grade 1 or better (grading system of the National Cancer Institute Cancer Therapy Evaluation Program (NCI-CTEP)); (4) twenty-four hour creatinine clearance of 60 ml/min or better; (5) liver function tests no more than twice the upper limit of normal; (6) normal complete blood cell count, differential, and platelet count; and (7) no prior radiotherapy, except for intraperitoneal P-32. Patient characteristics are listed in Table 1.

TABLE 1

| Patient Characteristics | | |
|---|---|---|
| | Median | Range |
| Age (years) | 52 | 35–70 |
| Karnofsky Performance Status (%) | 90 | 80–100 |
| Number of Prior Treatment Regimens | 2 | 1–2 |

Number of patients with:
Platinum-sensitive disease: 4
Platinum-resistant disease: 11
Extra-abdominal or liver disease: 5

Taxol was administered as a 24-hour continuous intravenous (IV) infusion that was delivered in a total volume of three liters of 5% dextrose injection, USP (i.e., one third of the total dose dissolved in one liter, which was administered during an eight hour period). Taxol was supplied by the Developmental Therapeutics Program of the National Cancer Institute. All patients were premedicated as follows: (1) dexamethasone 20 mg orally, 14 hours and 7 hours prior to taxol; and (2) cimetidine 300 mg IV and diphenhydramine 25 mg IV, 30 minutes prior to taxol. For the first two cycles of therapy, patients were monitored in the medical intensive care unit (ICU) during the taxol infusion and for 6 to 12 hours following completion of the infusion. All patients received subsequent cycles of therapy on the general medical oncology in-patient ward.

The G-CSF was self-administered subcutaneously by patients on a daily basis, beginning 24 hours after completion of the taxol infusion. A G-CSF dose of 10 µg/kg/day was used. The administration of G-CSF was continued until there was convincing evidence of bone marrow recovery from the taxol-induced nadir, which included a white blood cell (WBC) count of greater than 10,000 cells/mm$^3$ and a platelet count of greater than 50,000/mm$^3$. This was determined by checking WBC and platelet counts on a twice weekly basis.

Initially, three patients were entered onto protocol at each taxol dose level except for 170 mg/m$^2$ (two patients only). The taxol doses administered in this study were 170, 200, 250, and 300 mg/m$^2$, given once every three weeks. All toxicities were graded according to the NCI-CTEP criteria, with the exception of peripheral neuropathy which was graded as described previously herein. Nerve conduction studies were performed before commencing the taxol treatment in order to provide a baseline level in 12 patients. In two of these patients who developed clinical evidence of neuropathy, the studies were repeated on three occasions in case 1 and once in case 2. In all 12 patients, maximal motor and sensory conduction velocities and response amplitudes were recorded for the median or ulnar nerve in the upper limb and for the peroneal and sural nerves in the lower limb.

Dose limiting toxicity (DLT) was defined as any of the following criteria occurring in two of three patients treated at a given dose level: (1) reversible non-hematologic toxicity of at least grade 3; (2) irreversible non-hematologic toxicity of at least grade 2; or (3) the persistence of a nadir with an absolute granulocyte count of less than 500 cells/mm$^3$ or platelet count of less than 25,000/mm$^3$ for five days or more. Once DLT was reached (at 300 mg/m$_2$/21 days), four additional patients were treated at the dose level preceding the DLT, which was 250 mg/m$_2$/21 days.

Patients who had normalization of serum CA-125 levels and complete resolution of all assessable disease confirmed at peritoneoscopy Were assessed as having a clinical complete response to therapy (CCR). A partial response (PR) was designated for individuals experiencing a greater than 50% reduction in the sum of the products of the greatest perpendicular diameters of all measurable lesions that lasted at least one month. A minor response (MR) was defined as a greater than 25% but less than 50% reduction in the sum of the products of the greatest perpendicular diameters of all measurable lesions lasting at least one month. Patients with a less than 25% reduction in tumor volume after two cycles of therapy were considered to be nonresponders and were taken off therapy. Patients who experienced greater than 25% reduction in tumor volume and/or a more than 50% reduction in CA-125 level received two cycles beyond maximal response. Patients with CCR received two cycles beyond peritoneoscopy.

Fifteen patients received a total of 65 cycles of taxol therapy. All patients were considered assessable for toxicity. Table 2 lists all toxicities of grade 3 or greater associated with the therapeutic method of the present invention. Such toxicities included myelosuppression and peripheral neuropathy.

TABLE 2

Patient Events Stratified by Taxol Dose Level

| Patient Category | Number of Patients in Each Dose Level | | | |
|---|---|---|---|---|
| | 170 mg/m$^2$ | 200 mg/m$^2$ | 250 mg/m$^2$ | 300 mg/m$^2$ |
| Total Number of Patients Treated | 2 | 3 | 7 | 3 |
| Patients Receiving >1 cycle | 2 | 3 | 6 | 3 |
| Patients Requiring Dose Reduction or Delay | 0 | 0 | 2 | 2 |
| Patients With Granulocytopenia ≧ grade 3 | 0 | 2 | 6 | 1 |
| Patients With Thrombocytopenia ≧ grade 3 | 0 | 0 | 4 | 1 |
| Patients With Peripheral Neuropathy ≧ grade 3 | 0 | 0 | 1 | 2 |
| Total Number of Cycles Administered At This Dose | 14 | 20 | 25 | 6 |
| Total Number of Cycles Per Patient Started At This Dose Level (Includes Cycles of Dose Reduction) | 2,12 | 2,7,10 | 1,2,2,2, 2,4,7 | 3,4,8 |

Note: Toxicities that were non-dose-related included alopecia, myalgias, and asymptomatic bradycardia.

Although granulocytopenia occurred in spite of G-CSF support, this was always of brief duration (less than 5 days) and in no case necessitated taxol dose reduction. The thrombocytopenic episodes that occurred were also of brief duration and did not require platelet transfusions. In one patient, a platelet nadir taken during cycle 1 that was less than 20,000 cells/mm$^3$ for 3 days resulted in the lowering of the taxol dose from 250 mg/m$^2$ in cycle 1 to 200 mg/m$^2$ in cycle 2. The patient received two further cycles of therapy at a dose level of 200 mg/m$^2$, for a total of four cycles.

Only one patient received a single cycle of therapy. This patient experienced polymicrobial and candidal intraabdominal sepsis associated with free air in the abdominal space. The patient expired within 48 hours of the diagnosis of sepsis, in spite of vigorous antibiotic and pressor support in the ICU.

All patients received cycles 1 and 2 of taxol in the medical ICU of the Warren G. Magnuson Clinical Center of the National Institutes of Health, and were monitored for taxol-related cardiac effects. During the cycle 1 drug infusion, the heart rate fell below 60 beats per minute (bpm) in 10 individuals. For the group of 15, the mean nadir heart rate was 60±11 bpm (±standard error of the mean [SEM], range 46–84) and occurred at a mean SEM of 12±5 hours into therapy (range 1–21). During cycle 2, the heart rate fell below 60 bpm in 6 individuals (range 46–75) with a mean of 61±8 bpm and occurred at a mean 12±7 hours into therapy. There were no statistically significant differences between cycle 1 and cycle 2 in the incidence of bradycardia, or the degree or timing of the nadir heart rate.

In two patients, a substantial taxol-related event occurred that was of cardiac/cardiovascular origin. In one, a transient, asymptomatic, self-limited episode of Mobitz Type I (Wenckebach) second-degree heart block occurred 19 hours after the completion of the cycle 1 taxol infusion. In another, an episode of dizziness, nausea, and hypotension (systolic blood pressure of 66 mm Hg) occurred 6 hours after completion of the cycle 2 taxol infusion. Hypotension resolved promptly with a 500 ml bolus of IV 0.9% sodium chloride. Cardiac monitoring revealed a normal sinus rhythm that had a rate of 80; a subsequent 12-lead EKG and echocardiogram showed no abnormalities.

Although alopecia and grade 1 to 2 myalgias were observed in all patients, mucositis was observed in only two patients and was of grade 1 in both. Myalgias were readily controlled with mild analgesics.

Peripheral neuropathy of grade 3 was observed in three patients, and occurred in 2 of 3 patients receiving 300 mg/m$^2$ of taxol, thereby defining the DLT. This was manifested as numbness and tingling which developed simultaneously in fingers and toes, unsteadiness of gait, and difficulty with fine manipulation of the fingers, which manifested as difficulty buttoning clothing and putting on jewelry. Neurologic examination revealed impairment of vibration sense and partial loss of deep tendon reflexes. These three patients also had experienced clinical cisplatin-related peripheral neuropathy while receiving their prior anti-cancer treatment regimen, which was of a NCI-CTEP grade 0 or 1 at the time of taxol initiation. Several additional patients experienced mild paresthesias, manifested as tingling in a stocking and glove distribution, but without a functional deficit or loss of tendon reflexes. In these latter cases, the neurologic symptoms peaked 7 to 10 days after receiving taxol and persisted for 1 to 2 weeks beyond that time. Paresthesias generally improved prior to administration of the next cycle of drug.

In the two patients who were studied that developed grade 3 neuropathy, symptoms persisted for substantially longer periods (up to 6 months in case 1) and nerve conduction studies showed changes compared with the pretaxol studies. These are shown in Table 3.

TABLE 3

Nerve Conduction Studies in Two Patients with Grade 3 Polyneuropathy

| Modality | Nerve Studied | Case Number | MAP/SAP Amplitude Control | Lowest on Taxol | Percent Decrement |
|---|---|---|---|---|---|
| Motor | Ulnar | 1 | 6.9 mV | 7.1 mV | None |
| Motor | Peroneal | 1 | 3.9 mV | 1.9 mV | 49% |
| Motor | Median | 2 | 10.5 mV | 10.8 mV | None |
| Motor | Peroneal | 2 | 2.7 mV | 2.7 mV | None |
| Sensory | Ulnar | 1 | 19 μV | 6 μV | 62% |
| Sensory | Sural | 1 | 8 μV | 2 μV | 75% |
| Sensory | Median | 2 | 69 μV | 60 μV | 13% |
| Sensory | Sural | 2 | 32 μV | 18 μV | 44% |

Note: No changes were noted in maximal conduction velocity of any nerve studied in either patient.
Abbreviations: MAP = motor action potential; SAP = sensory action potential; mV = millivolts; μV = microvolts.

There was a significant decrease in the amplitudes of the sensory action potentials and the peroneal motor action potential in case 1, and in the sural sensory action potential in case 2. In contrast, the maximal conduction velocities were well preserved. Needle examination of the foot muscles in case 1 showed evidence of partial denervation not seen on the initial examination. These results suggest a mild sensory (in case 2) or sensorimotor (in case 1) polyneuropathy with features of axonal loss existing, but evidence of demyelination was lacking.

Based on clinical histories obtained from patients, it could neither be confirmed nor ruled out whether specific factors (e.g., prior cisplatin neurotoxicity, history of alcohol intake, etc.) were predisposing to taxol-related neurotoxicity in a statistically significant way. Taxol-related neurotoxicity is clinically very similar to cisplatin-related neurotoxicity.

Fourteen of the 15 patients were considered assessable for response after they had received two or more cycles of therapy. Five of 14 (36%) patients experienced an objective response to therapy (specifically, one complete response and four partial responses). Of the four partial responses, two patients had complete radiographic resolution of disease greater than 5 cm in dimension, and one had complete radiographic resolution of bulky liver disease. Of these three, one had a persistent elevation of CA-125 in the range of 45 to 135 units/ml (patient baseline >4,000; normal <35). Peritoneoscopy was attempted in the other two patients. One was not assessable by peritoneoscopy due to dense adhesions observed during the procedure; the other patient had no visible disease but random biopsies and washing results were positive for microscopic disease.

Five additional patients experienced a minor response, with reductions in tumor mass ranging from 30% to 46%. Four patients experienced progressive disease on therapy. The patient who died during the nadir of cycle 1 had documented bowel-wall disease at the time of initiation of therapy, and it is unclear whether her episode of intraabdominal sepsis occurred as a result of responding disease. Durations of response ranged from 11 weeks to more than 30 weeks. Median follow-up on the study was ten months. Disease response to therapy is summarized in Table 4.

TABLE 4

Disease Response Stratified by Dose Level

| Dose of Taxol (mg/m$^2$) | No. Patients Assessable For Response | No. CCR | No. PR | No. MR | No. NR |
|---|---|---|---|---|---|
| 170 | 2 | — | 1 | — | 1 |
| 200 | 3 | 1 | — | 1 | 1 |
| 250 | 6 | — | 1 | 3 | 2 |
| 300 | 3 | — | 2 | 1 | — |
| Totals | 14 | 1 | 4 | 5 | 4 |

Note: Response durations for CCR were 30+ weeks and for PR were 30 weeks, 25+ weeks, 23+ weeks, and 11 weeks.
Abbreviations: mg/m$^2$ = milligrams of drug per square meter of body surface area; CCR = clinical complete response; PR = partial response; MR = minor response; NR = no response.

With respect to prior therapy, 11 patients experienced progressive disease on, or relapsed within 6 months of, their most recent platinum-based chemotherapy regimen. These patients had disease considered to be platinum-resistant. Four patients had disease that recurred more than 6 months after their most recent platinum-based therapy, and were deemed to have platinum-sensitive disease. All responders were patients in the platinum-resistant group. Of the patients that experienced disease progression, none showed a decrease in serum CA-125 levels.

EXAMPLE 2

This example further illustrates the ability of the present invention to provide for the delivery of increased levels of taxol to patients with ovarian cancer. In particular, this example sets forth the results of a phase II study of patients with recurrent, platinum-refractory ovarian cancer who, at least initially, were placed on a taxol dosage regimen of 250 mg/m$^2$/ 21 days with G-CSF support in an amount of 10 μg/kg/day.

A total of 47 patients were included in this study. All patients had recurrent advanced stage epithelial ovarian cancer confirmed on histologic review at the Laboratory of Pathology, National Cancer Institute (NCI). Borderline, mixed, and germ cell histologies were excluded. Eligibility criteria included: performance status of ECOG 2 or better, bidimensionally measurable disease documented radiographically or by physical examination or intraperitoneal disease documented radiographically or by physical examination or intraperitoneal disease documented at peritoneoscopy at NCI, failure of at least one prior regimen of which one must have contained cisplatin or carboplatin, creatinine clearance of at least 45 ml/min and serum creatinine no greater than 1.5, neurologic toxicity of no greater than grade 1 by the Cancer Therapy Evaluation Program Common Toxicity Criteria, no concurrent medical illnesses requiring beta-adrenergic or calcium channel blockers, no history of myocardial infarction and normal electrocardiogram (EKG), adequate bone marrow reserve (WBC greater than 3000/µl, granulocyte count greater than 1500/µl, and platelets of at least 100,000/µl), serum transaminases no greater than twice the upper limits of normal, bilirubin no greater than 1.5 mg/dl, no prior marrow transplant regimen, and no prior external beam radiation therapy.

The characteristics of the patients in this study are provided in Table 5.

TABLE 5

Patient Characteristics

Age (years):
  Mean = 54
  Median = 55
  Range = 26–74
Extent of Disease:
  Intra-abdominal only: 28 (60%)
  Extra-abdominal and/or Liver Parenchyma: 19 (40%)
Histologic Type:
  Serous: 24 (51%)
  Poorly Differentiated: 20 (43%)
  Other: 3 (6%)
Number of Prior Treatment Regimens:

| No. of Regimens | No. of Patients |
|---|---|
| 1 | 11 (23%) |
| 2 | 16 (34%) |
| 3 | 8 (17%) |
| 4 | 7 (15%) |
| 5 | 3 (6%) |
| 6 | 2 (4%) |

Clinical Platinum Sensitivity:
  Sensitive: 5 (11%)
  Resistant: 42 (89%)

All but one patient had bulky measurable disease; that patient had small nodular disease which could be assessed only by peritoneoscopy. More than 40% of the patients had received three or more prior treatment regimens, and 89% of the patients were refractory to platinum as defined by progression on a platinum-containing regimen or experienced recurrence within six months of completing a platinum-containing regimen.

Pretreatment evaluation consisted of a physical examination, laboratory studies with CA-125, radiographic evaluation by CT scan, baseline electromyogram with nerve conduction velocity studies (EMG/NCV), creatinine clearance, chest radiograph, and EKG. On-study staging was completed within two weeks of starting therapy. Physical examination and laboratory evaluations were repeated with every cycle, except for CBC which was evaluated twice weekly. Patients underwent restaging every two cycles (i.e., every 6 weeks), which included the repetition of any radiographic studies that were abnormal upon entry. EMG/NCV studies were repeated as indicated to determine the presence of any progressive neurologic toxicity.

Taxol was supplied as a concentrated sterile solution (6 mg/ml in 5 ml ampules in Cremophor EL) by the Division of Cancer Treatment, NCI. The taxol was administered at a dose of 250 mg/m$^2$ as a continuous intravenous infusion in 5% dextrose over 24 hours.

Patients were monitored in the intensive care unit of the oncology inpatient unit during the 24 hour infusion and for six hours following completion of the taxol infusion. G-CSF was self-administered subcutaneously beginning 24 hours after the taxol infusion was completed. The G-CSF was supplied to the Division of Cancer Treatment by Amgen, Inc. (Thousand Oaks, Calif.). This G-CSF administration continued until the absolute granulocyte count of the patient was greater than 1500/µl for two consecutive days after the nadir (i.e., the total count for the two days was at least 3000/µl) or until the total white blood cell count was greater than 30,000/µl. Patients with responding disease or stable disease continued on the study and were reevaluated at two cycle intervals.

Taxol and/or its cremophor-ethanol vehicle have been demonstrated to cause hypersensitivity reactions and can cause cardiac dysrhythmias. Therefore, all cycles of taxol were given by continuous intravenous infusion over 24 hours with premedication. This premedication consisted of dexamethasone (20 mg orally or intravenously at 14 and 7 hours prior to taxol) and cimetidine (300 mg with diphenhydramine 50 mg intravenously 30 minutes prior to initiation of the taxol infusion). Each patient's first cycle of taxol was given in the medical intensive care unit, this allowed for continuous cardiac monitoring of the patient. Subsequent cycles of taxol were given on the inpatient oncology unit for patients having asymptomatic bradycardia or no cardiovascular toxicity on the first cycle. Patients manifesting second or third degree heart block had remaining cycles given in the intensive care unit with appropriate interventions. Antiemetics were given as needed.

In order to assess the results of the methodology of the present invention, the following definitions were developed and used in this study. A complete response (CR) was defined as patients having a complete resolution of disease as determined by both physical and radiographic examination as well as normalization of CA-125 lasting at least 4 weeks. A partial response (PR) patient was defined as having a greater than 50% reduction in the sum of the products of bidimensional measurements of all sites of disease as determined by both physical and radiographic analysis which lasted at least 4 weeks, and wherein no development of new lesions was observed. A minor response (MR) patient was defined as having greater than 25% but less than 50% reduction in the sum of the products of the perpendicular diameters of all measurable lesions and wherein no new sites of disease were observed. A stable disease (SD) was defined as patients having less than a 25% increase or less than a 25% reduction in sum of the product of the perpendicular diameters of all measurable lesions in response to therapy, without development of new lesions, for at least 4 weeks. Progressive disease (PD) was defined as patients having an increase of at least 25% in the sum of the products of the perpendicular diameters of all measurable lesions and/or the development of new lesions.

CA-125 levels were followed in all patients but were not used to define a patient's response except in one situation. If a patient had complete resolution of radiographic disease, but had an abnormal CA-125, that patient was considered to be a partial responder for purposes of this study.

During the first nine months of the study, taxol therapy was halted for nineteen patients two cycles after the patients attained their best response because of limitations in the drug supply. In these nineteen patients, the duration of the response could not be assessed. Further, in the early phase of the study, taxol was discontinued if an objective response was not observed following the first two cycles of therapy.

The responses of 44 of the 47 patients entered into the study were assessed and included in the results of this study as they had received at least two complete cycles of therapy. Of those three non-assessable patients, one had a life-threatening anaphylactoid reaction occurring three minutes into cycle 2 of taxol, and therapy was discontinued. The second patient died of polymicrobial and fungal peritonitis and sepsis during cycle 2 which was associated with a medical attempt at paracentesis. The third patient had a six unit vaginal bleed from a tumor during cycle 3. Taxol was interrupted in this patient for the administration of radiation therapy, after which taxol was subsequently restarted at a lower dose. This patient had a 90% reduction in tumor volume in response to the combined radiation and taxol therapy, but was not considered assessable for response. These patients who were considered non-assessable were nevertheless included in the evaluation of toxicities.

The first five patients treated in this study were administered starting dosages of taxol and G-CSF at levels of 250 mg/m$^2$/ 21 days and 10 µg/kg/day, respectively. However, after these dosages were administered, all five developed an initial episode of fever and neutropenia. These patients were subsequently treated with the same dose of taxol (250 mg/m$^2$) and G-CSF (10 µg/kg/day) in subsequent cycles. All five of the patients (100%) again developed neutropenia following this retreatment, and four of the five patients (80%) developed recurrent fever and neutropenia, including one patient who died from polymicrobial sepsis. Thus, patients who had one episode of fever and neutropenia were at high risk for another episode if no dose modifications of taxol or G-CSF were made. After this initial experience with a rigid taxol and G-CSF dosing schedule, the therapy was modified to decrease the risk of febrile neutropenia without reducing the dose intensity of taxol by providing for flexibility in the G-CSF dosage. More specifically, this was undertaken by increasing the dose of G-CSF administered on the next treatment cycle. The dose intensity of taxol was reduced only if a second episode of febrile neutropenia occurred despite the higher dose of G-CSF.

The particulars pertaining to the flexible G-CSF dosage regimen are as follows. Patients who had an episode of hematological toxicity (myelosuppression) characterized by a WBC of less than or equal to 1000/µl or neutrophils of less than or equal to 500/µl associated with fever greater than 101.5° F., had their G-CSF dosage increased to 15 or 20 µg/kg/day during subsequent cycles of therapy. If a patient had significant bone pain that required narcotic analgesics for relief, however, the G-CSF dosage was only increased to 15 µg/kg/day. In patients receiving the higher level of G-CSF (15 or 20 µg/kg/day) who developed a second episode of fever and neutropenia, the taxol dose intensity was reduced to 200 mg/m$^2$ on the next cycle. The dose of taxol was also reduced from 250 to 200 mg/m$^2$ in patients who experienced trade 3 non-hematological toxicity or thrombocytopenia. The dose of G-CSF was reduced by 5 µg/kg/day if severe bone pain occurred at these higher G-CSF dosage levels, i.e., at levels greater than or equal to 10 µg/kg/day.

In order to provide a comparison with the first five patients mentioned above who were placed upon a rigid taxol and G-CSF regimen, the remainder of the patients (42 of 47) were placed upon the flexible taxol and G-CSF dosage regimen described above. This regimen was started with taxol and G-CSF being administered at 250 mg/m2/day and 10 mg/kg/day, respectively. Nineteen patients (45%) continued at this dosage combination throughout therapy. Eighteen patients (43%) experienced fever and neutropenia (F+N+). Of these 18 patients, two patients did not receive further therapy because of stable or progressive disease while 16 patients had their G-CSF dose increased to 15 or 20 µg/kg/day for the next cycle. Two of these 16 patients were only increased to 15 µg/kg/day of G-CSF because of significant bone pain from G-CSF at the 10 µg/kg/day dosage level. Of the 16 patients receiving 250 mg/m$^2$/ 21 day of taxol and 15 or 20 µg/kg/day of G-CSF, 12 patients continued on that dose combination. Four of those 16 individuals had their taxol dosage reduced because of a second episode of febrile neutropenia. Four additional patients required taxol dose reductions as a result of developing thrombocytopenia or peripheral neuropathy. G-CSF was reduced to 5 µg/kg/day in a single patient who experienced severe bone pain secondary to G-CSF during her first cycle.

Table 6 summarizes the results associated with the various combinations of taxol and G-CSF used in this study.

TABLE 6

| | | | Hematologic Toxicity Seen In Patients Receiving Various Taxol/G-CSF Dose Combinations | | | | |
|---|---|---|---|---|---|---|---|
| G-CSF µg/kg | Taxol mg/m$^2$ | Total Pats.* | Total Cycles* | Cycles** AGC<500 | Patients** AGC<500 | Cycles** F+N+ | Patients** F+N+ |
| 10 | 250 | 42(100%) | 165(64%) | 57(35%) | 34(81%) | 18(7%) | 18(43%) |
| 20 | 250 | 14(33%) | 53(21%) | 25(10%) | 12(86%) | 6(11%) | 4(29%) |
| 10 | 200 | 4(10%) | 13(5%) | 6(46%) | 3(75%) | 1(8%) | 1(25%) |
| 20 | 200 | 5(12%) | 14(5%) | 5(35%) | 3(60%) | 2(14%) | 1(25%) |
| 15 | 250 | 2(5%) | 8(3%) | 0 | 0 | 0 | 0 |
| 5 | 250 | 1(2%) | 2(1%) | 0 | 0 | 0 | 0 |
| 20 | 150 | 1(2%) | 3(1%) | 0 | 0 | 0 | 0 |

*Percentage reflects percent of patients or cycles relative to total number of patients (42) and cycles (257) evaluated.
**Percentage reflects percent relative to total number evaluated at that dose combination.
Pats.: Patients
F+N+: Neutropenia accompanied by fever (febrile neutropenia).

As the data in Table 6 indicates, when cycles administered with 250 mg/m2/21 days of taxol and 10 g/kg/day of G-CSF are considered, 18 of 165 (11%) cycles were accompanied by fever. These 18 cycles were among 57 (35%) associated with neutropenia. At the higher G-CSF dose of 15 or 20 g/kg/day, six of 61 cycles (10%) were complicated by fever and neutropenia. These six cycles were among the 25 of 61 cycles (24%) associated with neutropenia.

Referencing this data to patients as opposed to cycles, Table 6 demonstrates that eighteen of 42 patients (43%) treated with 250 mg/m$^2$/ 21 days of taxol and 10 μg/kg/day of G-CSF had initial episodes of fever and neutropenia. These 18 patients were among 34 (53%) who developed neutropenia. If patients treated at a higher G-CSF dose of 15–20 μg/kg/day are considered, then four out of 16 (25%) had fever and neutropenia while receiving 5–20 μg/kg/day of G-CSF. Thus, the outcome in the total cohort studied was very similar to the outcome for the subset that was felt to be at high risk for recurrent neutropenia. In fact, the high risk group showed a slight reduction in the incidence of febrile neutropenia compared to the total cohort. This suggests that the high risk group may have been protected by the increase in the G-CSF dosage.

Table 7 analyzes the effect of G-CSF dosages on neutropenia for all patients treated with a taxol dose of 250 mg/m$^2$/ 21 days and either 10 or 20 μg/kg/day of G-CSF.

TABLE 7

Analysis Of G-CSF Effect On White Blood Cell (WBC) Toxicity At A Taxol Dose Of 250 mg/m$^2$/21 days

|  | No. of Cycles Studied* | Mean | Median | Range |
|---|---|---|---|---|
| 10 μg/kg G-CSF |  |  |  |  |
| Nadir (all cycles) | 130 | 1341 ± 1636 | 865 | 0–6232 |
| Day of Onset of Neutropenia in Neutropenic Cycles | 54 | 7 ± 0.8 | 7 | 5–9 |
| Nadirs in Neutropenic Cycles | 49 | 178 ± 158 | 162 | 0–494 |
| Duration of Neutropenia (Days) in Neutropenic Cycles | 49 | 1 ± 0.7 | 1 | 1–4 |
| 20 μg/kg G-CSF |  |  |  |  |
| Nadir (all cycles) | 42 | 1204 ± 1430 | 626 | 0–6536 |
| Day of Onset of Neutropenia in Neutropenic Cycles | 20 | 7 ± 1.1 | 7 | 6–11 |
| Nadirs in Neutropenic Cycles | 20 | 200 ± 155 | 191 | 0–493 |
| Duration of Neutropenia (Days) in Neutropenic Cycles | 20 | 1 ± 0.9 | 1 | 1–5 |

*Data is from all cycles where counts are available. For some patients followed at outlying hospitals, frequent blood counts were not obtained.

No significant differences were found in mean neutrophil nadir, day of onset of neutropenia, or duration of neutropenia. Complete blood counts were obtained on Mondays and Thursdays and were not obtained more frequently unless the patient developed fever. The reported duration of neutropenia may be an underestimation in some patients for this reason. However, when a patient developed fever, daily counts were obtained until fever and neutropenia resolved. Therefore, a cycle of therapy with documented fever included a more precisely documented WBC nadir. The average duration of neutropenia in patients receiving taxol (250 mg/m$^2$/ 21 days) and G-CSF (10 μg/kg/day) who developed febrile neutropenia was 2.0 ±1.1 days. Thus, even in patients who developed febrile neutropenia, the duration of neutropenia was brief.

G-CSF was administered for an average 7.2 ±1.6 days for patients who developed febrile neutropenia. No significant differences in the length of G-CSF administration were found between different cycles of therapy or between the two G-CSF dose levels.

Table 8 demonstrates that the number of prior therapies received did not have an impact on the development of fever during a neutropenic episode.

TABLE 8

The Presence Of Febrile Neutropenia During Cycle One (Taxol at 250 mg/m$^2$ and G-CSF at 10 μg/kg) Relative To The Number Of Prior Therapies Received

|  | F(+)N(+) | F(−)N(+) |
|---|---|---|
| No. of Patients | 20 (43%) | 27 (57%) |
| No. of Prior Therapies |  |  |
| Range | 1–5 | 1–6 |
| Median | 2 | 2 |
| Mean ± S.D. | 2.63 ± 1.3 | 2.53 ± 1.5 |

Note:
F(+) N(+): neutropenia with fever
F(−) N(+): neutropenia without fever

This use of flexible G-CSF dosing was determined to be successful in that it allowed patients who may have otherwise required dose reductions of taxol to receive continued therapy. In this study, the risk of recurrent febrile neutropenia did not differ significantly between patients who had a high risk of a second episode of neutropenia who were given 20 μg/kg/day doses of G-CSF, and patients having an average risk who were being administered 10 μg/kg/day of G-CSF. This suggests that there exists a protective effect associated with higher G-CSF dose levels in high risk patients.

One of the goals of this study was to observe the results obtained when the dose intensity of taxol was maintained at 250 mg/m$^2$/ 21 days (83.3 mg/m$^2$/ 7 days), (one cycle constituting 21 days). Therefore, cycles were given on a rigid schedule with delays being incurred only for extreme circumstances. Taxol dose was reduced when patients had severe non-neutropenic toxicity, or recurrent fever during neutropenia despite a modification in G-CSF dosage under the flexible dosing regimen described previously. As a result, the taxol dose intensity was maintained above 80% of the target dose for up to 14 consecutive cycles. The overall dose intensity for all cycles of therapy per patient provided a median dose intensity at the targeted 83.3 mg/m$^2$/ 7 days, while the average administered dose intensity was 79.1 mg/m2/7 days.

With specific regard to disease response, forty-four patients who received at least two cycles of therapy were deemed assessable. As seen in Table 9, twenty-one had objective responses to therapy documented by physical examination, radiographs, and peritoneoscopy.

TABLE 9

Disease Response Rates For Assessable Patients Receiving Dose Intense Taxol With G-CSF

| Response | No. of Patients | % of Cohort |
|---|---|---|
| CR | 6 | 14 |
| PR | 15 | 34 |
| MR | 5 | 11 |
| SD | 6 | 14 |

TABLE 9-continued

Disease Response Rates For Assessable Patients
Receiving Dose Intense Taxol With G-CSF

| Response | No. of Patients | % of Cohort |
|---|---|---|
| NR | 11 | 25 |

Six of these 21 responders (14% of the total) had complete resolution of their disease by physical examination, radiographs and CA-125; two of these six patients had negative second look peritoneoscopy. In two patients, peritoneoscopy was unsuccessful due to adhesions. Pathologic review of peritoneoscopy specimens was positive in two patients. Fifteen patients experienced partial responses to therapy with at least a 50% regression of disease as determined by physical examination or radiographs. The patients having a positive peritoneoscopy received four cycles of taxol after documentation of radiographic resolution of the disease (2 pre- and 2 post-peritoneoscopies). An additional five patients attained minor responses to therapy. The overall objective response rate was 48% (21/44, 95% CI: 33–63%).

As mentioned previously, during the early phase of the trial, the taxol drug supply was limited and therapy was therefore not continued for patients who did not attain at least a 30% disease regression or a 50% drop in CA-125 after the first two cycles of therapy or attained disease stabilization after reaching their best response (19 patients). The taxol supply was less restricted in the latter part of the study, which allowed for the observation of the time required to reach an objective response. Nineteen patients were treated until a patient demonstrated a complete clinical response (at which time therapy was discontinued) or there was uncovered evidence of disease progression. The median number of cycles required to reach an objective response was four, with a range of two to eight cycles. This demonstrates that many patients had a slow but continuous response to taxol treatment, underscoring the importance of careful evaluation and continued treatment until the best response is achieved.

Responding patients were analyzed for the duration of the response period using the Kaplan-Meier method. Median follow-up was eight months (3–21+ months). The median survival time for patients in the study was 11.5 months. Survival at one year was 45.3% (95% confidence interval; 25–67%).

As in Example 1, the dose-limiting toxicity encountered in this phase II study was sensory neuropathy. Forty-seven patients were assessable for toxicity. The breakdown of toxicities by type and severity is provided in Table 10.

TABLE 10

Toxicities Experienced And Dose Reduction
Requirements During Dose Intense Taxol With
G-CSF Support

| Toxicity | Grade 1 & 2 No. (%) | Grade 3 & 4 No. (%) | Taxol DR No. (%) | G-CSF DR No. (%) |
|---|---|---|---|---|
| Hematologic | | | | |
| Granulocytes | 1 (2) | 46 (98) | 4 (9) | — |
| Platelets | 24 (51) | 19 (40) | 2 (4) | — |
| Anemia | 17 (47) | 30 (47) | — | — |
| Neurologic | 36 (77) | 3 (6) | 3 (6) | — |
| Cardiac | 35 (74) | — | — | — |
| Hypersensitivity | | | | |
| Reactions | 31 (66) | 2 (4) | — | — |
| Mucositis | 31 (66) | 3 (6) | — | — |
| Myalgias | 43 | — | — | — |
| Diarrhea | 29 | 2 (4) | — | — |
| Vomiting | 23 | — | — | — |
| Alopecia | 38 | — | — | — |
| Constitutional | 43 | 4 (9) | — | — |
| Bone Pain | — | 3 (6) | — | 3 (6) |

Myelosuppression was the predominant type of grade 3 and 4 toxicity. The median time of neutrophil nadir was day 7 (range day 5–11), and G-CSF was administered for a median of 8 days beginning 24 hours after the completion of the taxol infusion (mean 7.6, range 3–12). Dose escalation of G-CSF was necessary to maintain taxol dose intensity (250 mg/m$^2$/ 21 days) in 16 patients. Only 4 patients required a taxol dosage reduction to 200 mg/m$^2$/ 21 days due to fever during neutropenia. This fever occurred despite an increase in the G-CSF dosages. Two patients required taxol dose reduction because they demonstrated grade 4 thrombocytopenia, i.e., a myelosuppressive event, defined for this study as a platelet count of less than 25,000/µl for at least 5 days. Neither of these two patients required platelet transfusions after the taxol dose was reduced to 200 mg/m$^2$/ 21 days. Twenty-six patients (55%) required red blood cell transfusions. One patient was maintained on erythropoietin injections to avoid transfusions due to prior development of multiple transfusion-related antibodies. While dose intense taxol was associated with grade 3 and 4 hematologic toxicities in 98% of patients, these toxicities were short-lived and required taxol dose reduction in only 6 of 47 (13%) patients. Once reduced, however, taxol was not escalated back to the targeted dose. The median duration of absolute neutropenia and of grade 4 thrombocytopenia, when they occurred, was one day. There was one treatment related death due to polymicrobial sepsis (2%).

Taxol-induced peripheral neuropathy resulted in a dose reduction in only 3 patients. All had been previously treated with cisplatin and had received 5, 3, and 3 prior treatment regimens, respectively. All had CTEP grade 1 neuropathy at the initiation of taxol treatment. Taxol-induced neuropathy consisted primarily of abnormalities of proprioception and mild distal sensory polyneuropathy with paresthesias. Generally, neuropathic symptoms peaked midcycle and returned to baseline by day one of the subsequent cycle. However, these three patients had persistent residual mild complaints. Neuropathy stabilized after taxol dose reduction and, in most patients, began to resolve shortly after taxol was discontinued. Mild ototoxicity was seen in 5 of 47 patients (11%).

Cardiac toxicities were also observed. Asymptomatic sinus bradycardia was the predominant cardiac finding, occurring in 34% of the patients during cycle 1. The median nadir heart rate was 52 bpm (range: 38–59 bpm). Two of 47 patients (4%) experienced first degree atrioventricular block, 2 (4%) had Mobitz I block, and 2 (4%) had Mobitz II block. No episodes of complete heart block were seen in these 47 patients. Supraventricular tachycardia was seen in two patients, and rapid atrial fibrillation requiring digitalization was seen in one patient on two occasions. Premature atrial, junctional, and premature ventricular beats and ventricular bigeminy were rarely observed. All arrhythmias and conduction disturbances were asymptomatic.

Myalgias and arthralgias (grades 1 and 2) occurring within the first 10 days of each cycle were experienced by less than 50% of patients, and all were mild and abated rapidly. G-CSF doses were modified for bone pain in two patients. Mucositis was exhibited, but was minimal and not dose-limiting; it did not necessitate dose reduction in any patient. Two patients had hypersensitivity reactions. In one patient, bronchospasm developed three minutes into the second cycle of taxol and rapidly progressed to an upper airway obstruction which was associated with flushing and subsequent short runs of ventricular tachycardia. Administration of epinephrine was required to reverse the reaction. The patient did not have sequelae but was not retreated with taxol. The second patient had flushing, pruritic maculopapular rash, and bradycardia with her first cycle of taxol. A desensitization approach of slow taxol dose escalation was subsequently used successfully and she had a total of four cycles of therapy before attaining her best response. Overall, taxol was well tolerated, with only 9 of 47 patients (19%) requiring taxol dose reduction to 200 $mg/m^2$/ 21 days. No patients required taxol dose reductions below 200 $mg/m^2$/ 21 days.

A statistical comparison of the response rate of the current phase II study was made against the published ovarian cancer taxol data of Einzig with a response rate of 21% (Einzig et al., *Cancer Treat. Res.*, 58, 89–100 (1991)), McGuire et al. with a response rate of 33% (McGuire et al., *Ann. Int. Med.*, 111, 273–79 (1992)), and the Gynecologic Oncology Group with a response rate of 36% (Thigpen et al., *Proc. ASCO*, 9, 156 (1990)). These three combined studies show that 33 of 110 patients (30%) responded to taxol given without G-CSF, compared with 21 of 44 patients (48%) in the present phase II study responding to taxol given with G-CSF at the administered dose intensity of 83.3 $mg/m^2$/ 7 days. Bearing in mind the possible difficulties in comparison of nonrandomized patient cohorts to one another, a statistically significant difference was demonstrated by comparison of the present trial with those described above ($P_2$ =0.037, $X^2$ test). Thus, the 48% response rate achieved in this study indicates that increased taxol dose intensity is associated with increased response rate in platinum-refractory patients having advanced stage ovarian cancer which is independent of patient age and degree of prior therapy.

Moreover, the use of a flexible G-CSF dosing regimen was successful in that it allowed patients who may have otherwise required dose reductions of taxol to receive continued therapy at the higher taxol dosage level.

The phase I study which forms the basis, in whole or in part, of Example 1 was published in Sarosy et al., *Journal of Clinical Oncology*, 10 (7), 1165–70 (July 1992). The results of the phase II study which forms the basis, in whole or in part, of Example 2 has been submitted for publication in the form of two separate papers. These references, as well as all of the references cited herein, are hereby incorporated in their entireties by reference.

While this invention has been described with an emphasis upon a preferred embodiment, it will be obvious to those of ordinary skill in the art that variations of the preferred method may be used and that it is intended that the invention may be practiced otherwise than as specifically described herein. Accordingly, this invention includes all modifications encompassed within the spirit and scope of the invention as defined by the following claims.

What is claimed is:

1. A method of treating a host being treated with taxol in an amount sufficient to cause a side effect selected from the group consisting of myelosupression, mucositis, and peripheral neuropathy, which method comprises administering to said host granulocyte colony-stimulating factor in an amount effective to alleviate or prevent said side effect.

2. The method of claim 1, wherein said host is being treated with taxol in an amount exceeding about 175 $mg/m^2$/ 21 days.

3. A method of claim 1, wherein said side effect is myelosuppression or mucositis.

4. The method of claim 3, wherein said granulocyte colony-stimulating factor is administered in an amount of at least about 5 µg/kg/day.

5. The method of claim 4, wherein said granulocyte colony-stimulating factor is administered in an amount of about 10 to about 20 µg/kg/day.

6. The method of claim 1, wherein said host is being treated with taxol once every three weeks and said granulocyte colony-stimulating factor is administered daily for at least seven days following the taxol treatment.

7. The method of claim 6 wherein said host is being treated with taxol in an amount of about 200 to about 250 $mg/m^2$/ 21 days.

8. The method of claim 1, wherein said host is being treated with taxol to treat a cancerous tumor.

9. The method of claim 8, wherein said cancerous tumor is a breast, lung or ovarian tumor.

10. The method of claim 9, wherein said cancerous tumor is an ovarian tumor.

11. The method of claim 10, wherein said host is being treated with taxol in an amount exceeding about 175 $mg/m^2$/ 21 days.

12. The method of claim 11, wherein said granulocyte colony-stimulating factor is administered in an amount of at least about 5 µg/kg/day.

13. The method of claim 12, wherein said granulocyte colony-stimulating factor is administered in an amount of about 10 to about 20 µg/kg/day.

14. The method of claim 13, wherein said host is being treated with taxol once every three weeks and said granulocyte colony-stimulating factor is administered daily for at least seven days following the taxol treatment.

15. The method of claim 14, wherein said host is being treated with taxol in an amount of about 200 to about 250 $mg/m^2$/ 21 days.

\* \* \* \* \*